(12) United States Patent
Derval et al.

(10) Patent No.: US 11,173,280 B2
(45) Date of Patent: Nov. 16, 2021

(54) CATHETER, MEDICAL DEVICE FOR THE INTRODUCTION OF A TREATMENT SOLUTION

(71) Applicants: UNIVERSITE DE BORDEAUX, Bordeaux (FR); CENTRE HOSPITALIER UNIVERSITAIRE DE BORDEAUX, Talence (FR); FONDATION BORDEAUX UNIVERSITÉ, Bordeaux (FR); INSTITUT NATIONAL DE LA SANTE ET DE LA RECHERCHE MEDICALE—INSERM, Paris (FR)

(72) Inventors: Nicolas Derval, Bordeaux (FR); Pierre Jais, Saint Medard en Jalles (FR); Arnaud Denis, Bordeaux (FR); Thomas Pambrun, Talence (FR); Josselin Duchateau, Talence (FR)

(73) Assignees: UNIVERSITE DE BORDEAUX, Bordeaux (FR); CENTRE HOSPITALIER UNIVERSITAIRE DE BORDEAUX, Talence (FR); FONDATION BORDEAUX UNIVERSITE, Bordeaux (FR); INSTITUT NATIONAL DE LA SANTE ET DE LA RECHERCHE MEDICALE—INSERM, Paris (FR)

(*) Notice: Subject to any disclaimer, the term of this patent is extended or adjusted under 35 U.S.C. 154(b) by 0 days.

(21) Appl. No.: 17/052,436

(22) PCT Filed: May 2, 2019

(86) PCT No.: PCT/EP2019/061212
§ 371 (c)(1),
(2) Date: Nov. 2, 2020

(87) PCT Pub. No.: WO2019/211363
PCT Pub. Date: Nov. 7, 2019

(65) Prior Publication Data
US 2021/0162186 A1    Jun. 3, 2021

(30) Foreign Application Priority Data
May 4, 2018    (FR) .................................... 1800426

(51) Int. Cl.
*A61M 25/00* (2006.01)
*A61M 25/01* (2006.01)
*A61M 25/10* (2013.01)

(52) U.S. Cl.
CPC ...... *A61M 25/0068* (2013.01); *A61M 25/008* (2013.01); *A61M 25/0069* (2013.01);
(Continued)

(58) Field of Classification Search
CPC ........ A61M 2025/1045; A61M 25/003; A61M 25/0067; A61M 25/0069; A61M 25/0068;
(Continued)

(56) References Cited

U.S. PATENT DOCUMENTS 5,827,268 A * 10/1998 Laufer ............... A61B 18/1492
606/28
6,416,493 B1 * 7/2002 Del Giglio ......... A61M 25/1011
600/381

(Continued)

FOREIGN PATENT DOCUMENTS

WO    WO 2007/027830 A1    3/2007
WO    WO 2009/135174 A1    11/2009

OTHER PUBLICATIONS

Written Opinion of the International Searching Authority as issued in International Patent Application No. PCT/EP2019/061212, dated Sep. 3, 2020.
(Continued)

*Primary Examiner* — Nathan R Price
*Assistant Examiner* — Melissa A Snyder

(74) *Attorney, Agent, or Firm* — Pillsbury Winthrop Shaw Pittman LLP

(57) ABSTRACT

A medical device includes a catheter, which includes a first lumen for injection of a first volume of a treatment solution, the first lumen opening out at the distal end of the catheter; and a junction element extending the first lumen at the end of the catheter including a diameter at the distal end thereof less than the diameter of the catheter.

15 Claims, 6 Drawing Sheets

(52) U.S. Cl.
CPC .......... *A61M 25/01* (2013.01); *A61M 25/1011* (2013.01); *A61M 2025/0004* (2013.01); *A61M 2025/105* (2013.01); *A61M 2025/1045* (2013.01)

(58) Field of Classification Search
CPC .......... A61M 25/0082; A61B 17/12122; A61B 17/11; A61B 17/12022; A61B 17/1204; A61B 17/0057
See application file for complete search history.

(56) References Cited

U.S. PATENT DOCUMENTS

| 2011/0152760 | A1* | 6/2011 | Parker .............. A61M 25/0074 604/96.01 |
| 2012/0179102 | A1 | 7/2012 | Blanchard et al. |
| 2014/0148889 | A1 | 5/2014 | Deshmukh et al. |
| 2014/0180255 | A1 | 6/2014 | Leblanc et al. |

OTHER PUBLICATIONS

International Search Report as issued in International Patent Application No. PCT/EP2019/061212, dated Aug. 28, 2019.

\* cited by examiner

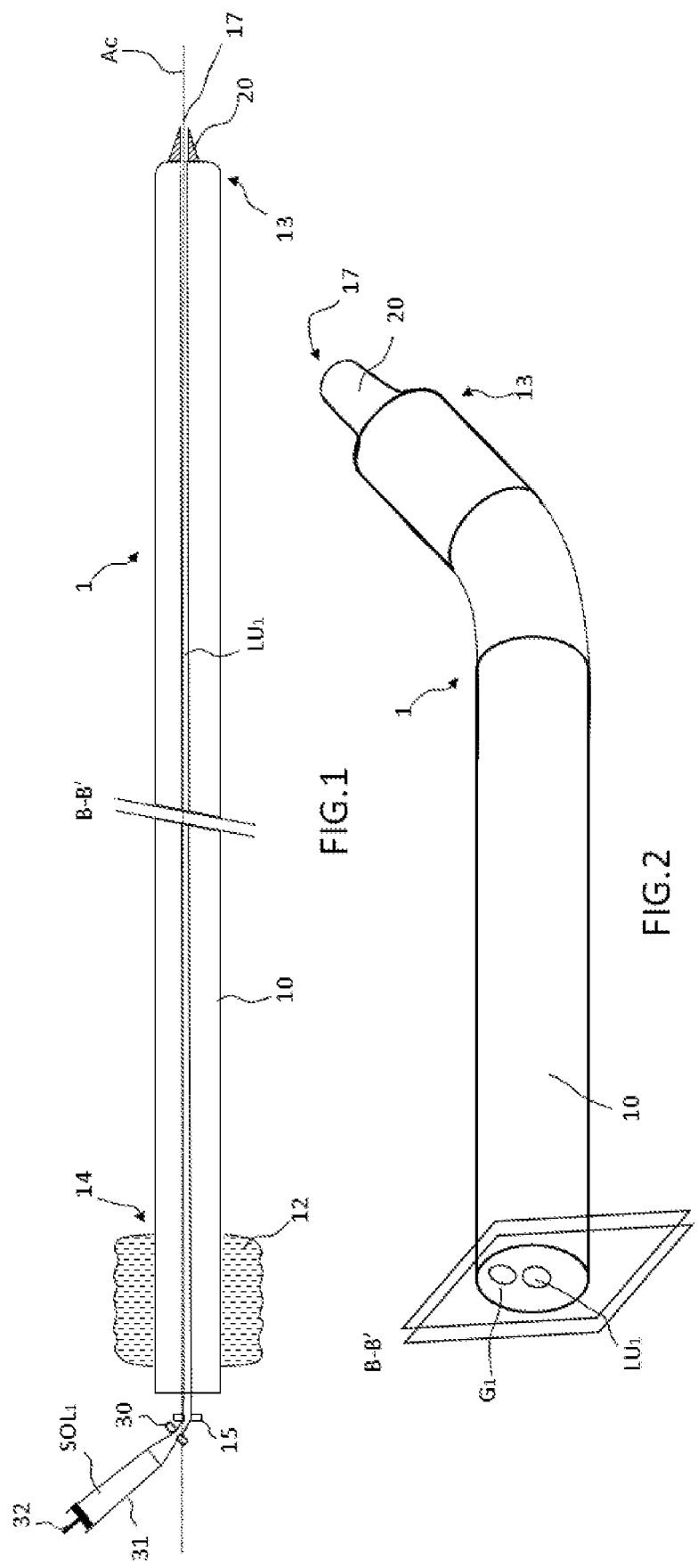

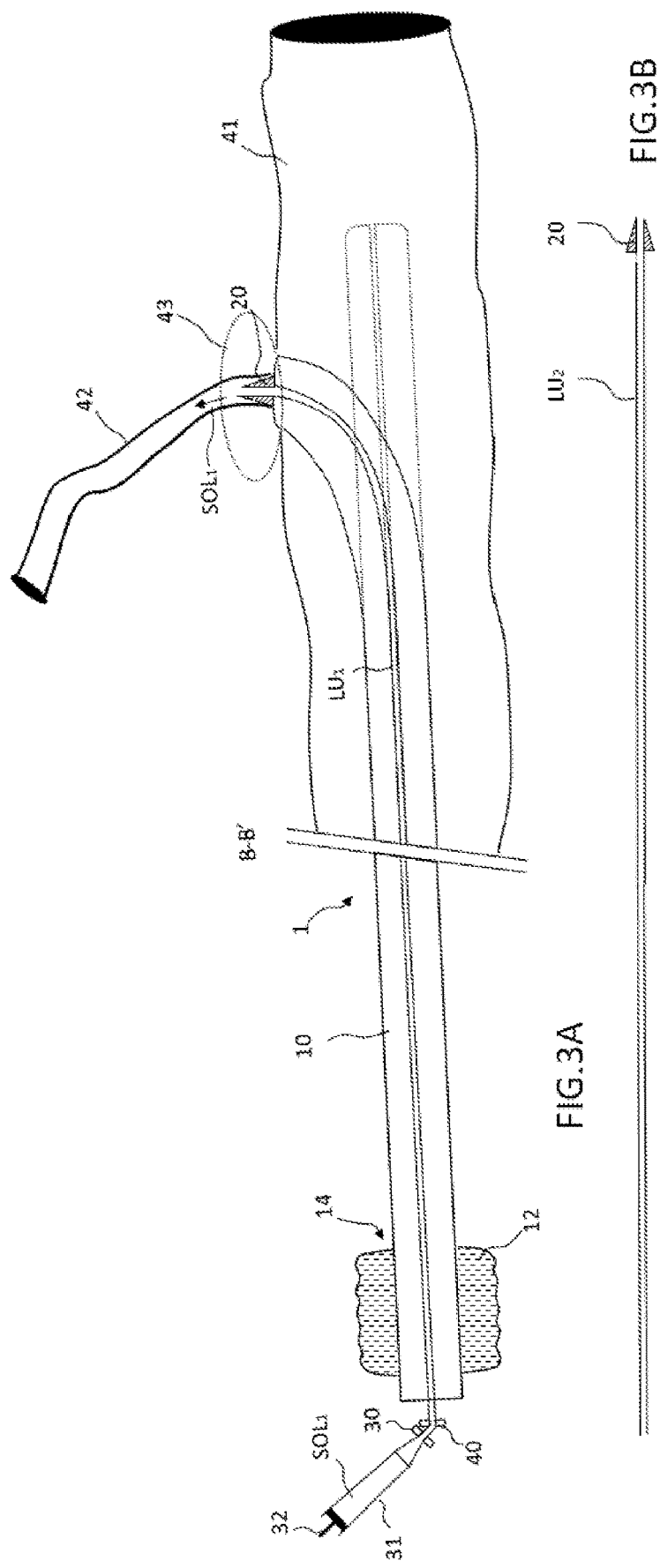

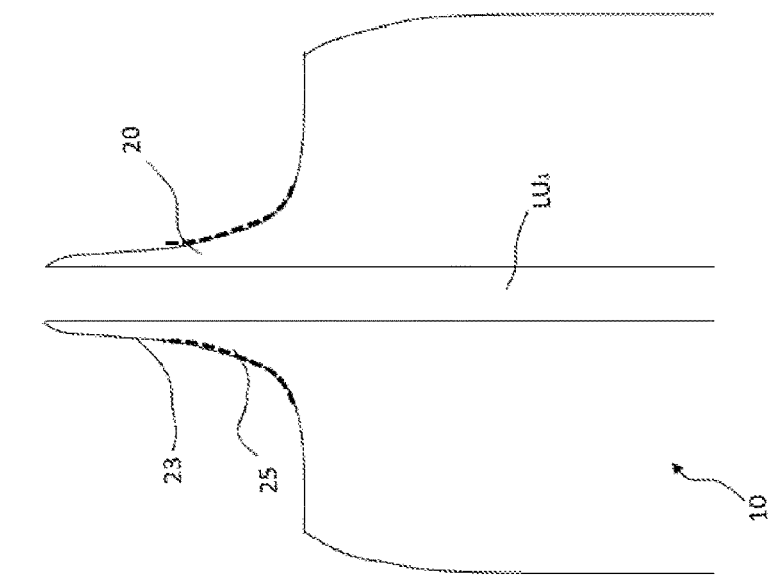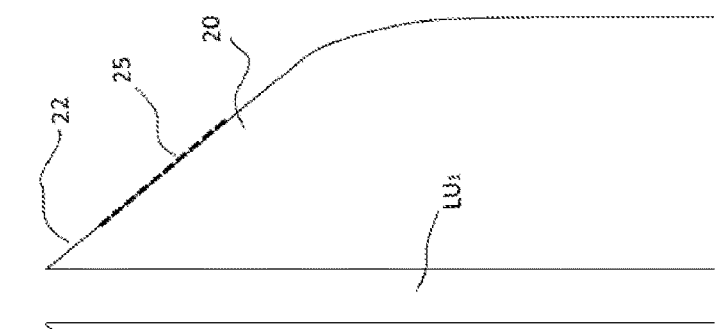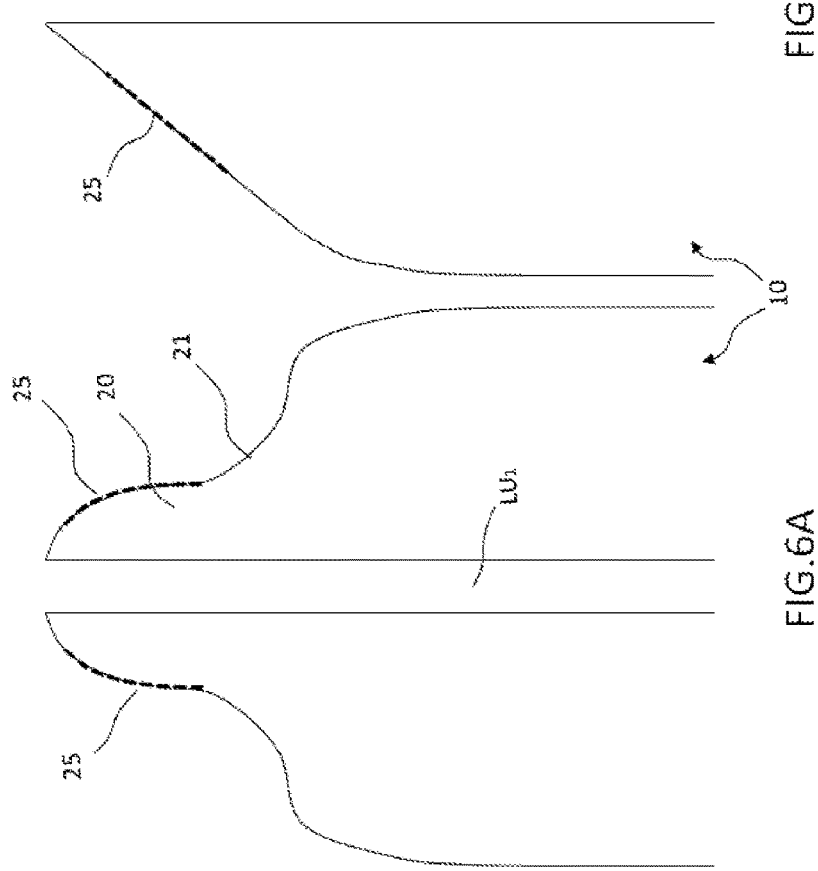

CATHETER, MEDICAL DEVICE FOR THE INTRODUCTION OF A TREATMENT SOLUTION

CROSS-REFERENCE TO RELATED APPLICATIONS

This application is the U.S. National Stage of PCT/EP2019/061212, filed May 2, 2019, which in turn claims priority to French patent application number 1800426 filed May 4, 2018. The content of these applications are incorporated herein by reference in their entireties.

FIELD

The field of the invention relates to devices for introducing a solution into a channel of the human body, more particularly vessels and in particular the vein of Marshall. The field of the invention relates to devices for the treatment of certain cardiac pathologies. More particularly, the field of the invention relates to that of catheters comprising a means for directing a solution to be injected into a channel for example of the vein of Marshall type.

STATE OF THE ART

Today, the vein of Marshall is involved in the causes of the occurrence of cardiac pathologies of the cardiac fibrillation type such as atrial fibrillation, called AF. The vein of Marshall is a vein of the heart that a priori is not necessary, but due to its implication in the occurrence of certain pathologies, it is treated during the execution of an act of interventional cardiology at the heart.

Atrial fibrillation AF is an arrhythmia defined by a chaotic activation of the atria. It is triggered by atrial extrasystoles that initiate multiple and variable re-entries. The pulmonary veins, source of extrasystoles and a substrate for the re-entries, are recognized as the fundamental structures at the initiation and in the maintaining of atrial fibrillation. They are therefore the main target of the ablation. Other structures have similar characteristics: superior vena cava, coronary sinus, ligament of Marshall. Although the first two can be treated by the ablation, the ligament of Marshall is not readily accessible by this type of treatment.

The ligament of Marshall is an embryonic remnant resulting from the involution of the left superior vena cava and the musculature thereof. The incomplete apoptosis of the venous musculature leads to the persistence of several muscular connections between the endocardium and the epicardium. The ligament of Marshall is therefore comprised of a venous network of small caliber, also called "vein of Marshall", closely associated with a muscular arborization. This complex structure is propitious to the initiation and to the maintaining of the atrial fibrillation through automaticity and re-entry mechanisms. Winding between the left pulmonary veins and the left atrium, the vein of Marshall joins with the great cardiac vein to anastomose in the coronary sinus. As with all veins, it is often subject to anatomical path variations.

Because of the fact that it is difficult to treat the vein of Marshall by endocardial ablation—in particular because it is electrically insulated in a fat mass—or epicardial ablation (its very limited diameter does not allow for the introduction of an ablation catheter), other treatment techniques have been investigated.

One of the treatment methods used to date to reduce the implication of the vein of Marshall in the appearance of cardiac fibrillation is the introduction of a solution of the alcohol type into the vein.

Currently, there are catheters for introducing a treatment solution into the vein of Marshall. The existing catheters generally have a main lumen and a second lumen guided to be introduced into the vein of Marshall. However in order to secure the handling and to ensure that the second lumen is indeed introduced, it is necessary for a surgeon or an operator to sufficiently introduce the lumen inside the vein of Marshall.

This action has for consequence an impossibility of treating the zone of the vein located at the anastomosis of the latter with the main vein of the network in which the lumen is introduced. Consequently, the vein of Marshall is partially treated and most often the symptoms are only partially removed.

This problem is not localized to the sole case of the vein of Marshall, there is a need for a catheter and/or an element allowing for the introduction of a treatment solution in veins of small diameters and that open out onto another vein making it possible to treat the anastomosis zone of the vessel 41 and of the vessel 42.

SUMMARY OF THE INVENTION

The method of the invention makes it possible to resolve the aforementioned problems.

According to an aspect the invention relates to a medical device comprising:
  A catheter characterized in that it comprises a first lumen for injection of a first volume of a treatment solution, the first lumen opening out at the distal end of the catheter;
  A junction element extending the first lumen at the end of the catheter comprising a diameter at the distal end thereof less than the diameter of the catheter.

An advantage is to allow for the introduction of a volume of alcohol into a localized region inside the vein of Marshall and at the anastomosis thereof while still guaranteeing a seal of the treated zone thanks to a junction element of the catheter.

According to an embodiment, the catheter can be deformable and the deformation can be controlled.

According to an embodiment, said junction element is intended to cooperate with an anastomosis zone of a first vessel with a second vessel. The cooperation extends to form in particular a sealed contact between the junction element and the wall of the anastomosis zone.

According to an embodiment, the junction element is intended to form a sealed circumferential contact with an anastomosis zone of two vessels.

According to an embodiment, the junction element comprises a positioning ring intended to form a bearing surface in contact with the anastomosis zone, the diameter of the positioning ring being greater than the diameter of the catheter.

According to an embodiment the junction element comprises two electrodes arranged at the distal end thereof.

According to an embodiment, the body of the catheter comprises a plurality of electrodes arranged on at least one portion of the circumference thereof.

According to an embodiment, the device comprises a first positioning balloon arranged on the wall of the catheter and intended to create a first sealed border with the wall of a first vessel.

According to an embodiment, the device comprises a second positioning balloon arranged on the wall of the catheter and intended to create a second sealed border with a portion of the wall of the first vessel.

According to an embodiment, the junction element comprises a length comprised between 2 mm and 2 cm. An advantage is to adapt to different geometries of anastomosis and diameter of the coronary sinus and of the vein of Marshall.

According to an embodiment, the junction element comprises a portion having a circumferential edge intended to bear against the walls of a vessel. An advantage is to improve the seal of the zone to be treated by a good contact between the junction element and the wall of a vessel or of an anastomosis zone.

According to an embodiment, the junction element comprises a profile that has a concave or straight portion extending from the distal end of the catheter in the direction of the distal end of the junction element.

According to an embodiment, the junction element comprises a profile that has a substantial conical shape. An advantage is to allow for a sinking of the end of the catheter adapting to different geometries of the vessels treated.

According to an embodiment, the junction element comprises a rounded distal end. An advantage is to ensure a good seal while still limiting damage to the tissues.

According to an embodiment, the junction element is made from a deformable material comprising a ductibility that is higher than a predefined threshold.

According to an embodiment, the junction element is made from a deformable material comprising an elasticity that is higher than a predefined threshold.

According to an embodiment, the junction element comprises a profile of which the diameter varies so as to form a sealed wall between a first vessel and a second vessel when the distal end of the catheter is positioned bearing against the wall of the vessel.

According to an embodiment, the catheter comprises at least one electrode arranged at the distal surface of the body of the catheter making it possible to record the electrical activity in the vessel.

According to an embodiment, the first lumen comprises a diameter comprised between 2 F and 5 F, preferably 4 F.

According to another aspect, the invention relates to a usage of a device of the invention for the treatment of the vein of Marshall and of the anastomosis thereof. The treatment relates in particular to the alcoholization of this region, in particular in the objective of carrying out a chemical ablation.

BRIEF DESCRIPTION OF THE FIGURES

Other characteristics and advantages of the invention shall appear when reading the following detailed description, in reference to the accompanying figures, that show:

FIG. 1: a cross-section view along a longitudinal plane of an embodiment of a device of the invention;

FIG. 2: a 3D view of an embodiment of a device of the invention;

FIG. 3A: an embodiment of a device of the invention arranged in the vicinity of the anastomosis of the vessels 42 and 41;

FIG. 3B: an embodiment of a lumen comprising a termination forming an appendix;

FIGS. 6A, 6B, 6C: different embodiments of the junction element extending the distal end of the catheter of the invention;

DESCRIPTION

FIG. 1 shows an embodiment of a device of the invention along a longitudinal cross-section. The device 1 comprises a catheter 10 provided with a first lumen $LU_1$. The longitudinal cross-section shows an example of a catheter 10 that comprises a coaxial lumen $LU_1$.

Lumen $LU_1$

Figure 5:
FIG. 5: a three-dimensional representation of a heart on the surface of which the vein of Marshall is shown.

FIG. 3A diagrammatically shows the device of the invention arranged in a first vessel 41. The catheter 10 comprises a lumen $LU_1$ making it possible to convey, for example, a volume of a first solution $SOL_1$ intended to penetrate into a second vessel 42, such as a vein. The invention is particularly advantageous when it is applied to the introduction of a volume of liquid $SOL_1$ into the vein of Marshall 42. The device 1 of the invention makes it possible to reach the anastomosis 43 of the vein of Marshall 42 with sufficient precision so that the solution $SOL_1$ can penetrate into said vein. FIG. 5 shows a three-dimensional view of the vein of Marshall 42 at the surface of the myocardium. In a particular application case, the vessel 41 is the coronary sinus and the vessel 42 is the vein of Marshall.

According to an embodiment, the solution $SOL_1$ injected is an alcohol solution. An advantage is to treat the zone close to the anastomosis 43 which could not be carried out with the solutions addressed to the problem of the AF.

According to another example, the solution $SOL_1$ injected is an iodine solution. An advantage is to make it possible to improve the quality of images acquired by a medical imaging system. An interest is to have a single catheter 10 that makes it possible to provide different functions ranging from the positioning of the catheter 10 to the treating of the zone to be treated.

FIG. 1 shows an injector 31 comprising a solution $SOL_1$ intended to be injected into a vessel 42 of the human body. A piston 32 is shown so as to illustrate the function aiming to engage the solution $SOL_1$ into the lumen $LU_1$. A valve 30 makes it possible in this example to open or not the passage to a volume of a solution $SOL_1$ to be transmitted. Furthermore, the valve 30 can make it possible to remove a volume of air and/or to control the pressure inside the lumen $LU_1$. Other embodiments can be considered so as to generate a controlled pressure of the solution $SOL_1$ so that it can be injected into the zone to be treated 43 by the lumen $LU_1$ and the appendix 20 extending the lumen $LU_1$.

According to another example, the first lumen $LU_1$ allows for the passage of a guide to direct the catheter 10 until it reaches the anastomosis of the vessel 42. An advantage is to make it possible to reach, for example, the inside of the vein of Marshall using a guide.

According to an example of a treatment method, the catheter 10 of the invention makes it possible to chain a first treatment at the anastomosis 43 and a second treatment inside the vessel 42, for example, thanks to a second lumen $LU_2$, such as an angioplasty balloon, able to be displaced within the first lumen $LU_1$ and of which the diameter does not exceed that of the appendix 20. FIG. 3B shows a case where the second lumen $LU_2$ comprises a termination that forms an appendix 20, such as a termination with a conical shape or that has a triangular section.

According to an embodiment, the first lumen $LU_1$ is a lumen of diameter 4 F.

FIG. 3A shows, indeed, a vein of Marshall 42 opening out onto a vein 41. The catheter 10 is introduced into the vein 41 in such a way as to have the outlet 17 of the distal end of the appendix 20 in the anastomosis of the vein of Marshall 42. For this purpose, the catheter 10 was deflected and has a deformation that was able to be controlled using a proximal handle 12. So as to illustrate the deformation function of the catheter 10, the non-deformed trace of the catheter 10 is retained in FIG. 3A.

When the end 17 of the appendix 20 is well positioned with respect to the anastomosis of the vessel 42, i.e. making it possible to ensure the occlusion thereof and the seal thereof, the solution $SOL_1$ then flows in the vein of Marshall 42. An advantage of the invention is to make it possible to treat the proximal end of the vessel 42, i.e. the zone 43 that would not have been treated if an arm of a member of the catheter 10 had penetrated into the vein 42.

Junction Element

According to an embodiment, the device 1 comprises a junction element 20 that forms a distal appendix that extends the lumen $LU_1$ which is integrated into the catheter 10.

The junction element 20 can be fixed to the catheter 10 in different ways. It can be screwed or snap-fit for example if the distal end 13 of the catheter 10 provides a suitable fastening. According to another embodiment, the appendix is welded or glued in such a way as to form a single secured part of the catheter 10.

Figure 7A:
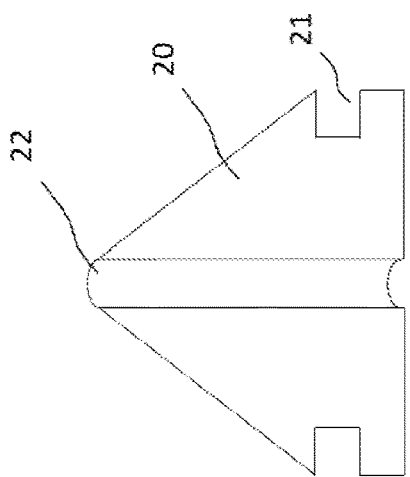
FIGS. 7A, 7B: an example of a connection between a junction element and a catheter of the invention.
Figure 7B:
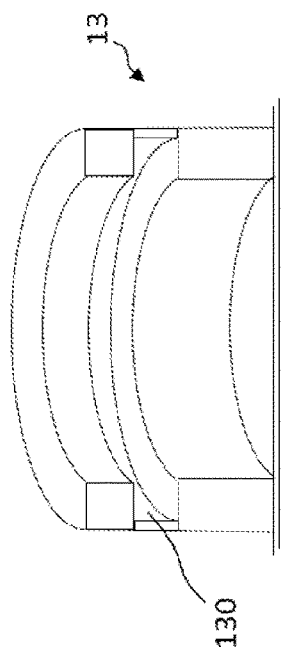

FIG. 7A shows an embodiment wherein the junction element 20 comprises a channel 22 that extends the lumen $LU_1$. It further comprises a circumferential groove 21 intended to cooperate with an internal groove 130 of the distal end 13 of the catheter 10 of FIG. 7B. In this embodiment, the junction element 20 can be made from a slightly deformable material so as to be able to be inserted and provide the occlusion and the seal. According to this embodiment, seals can be added and a gluing can be carried out in order to reinforce the integral connection between the junction element 20 and the catheter 10.

Other embodiments can be considered in the framework of the invention.

According to different embodiments, the junction element 20 can comprise different shapes so as to provide a first function of a seal between the vessel 41 and the vessel 42, in particular when a treatment solution is injected into the vessel 42. An interest is to maintain the distal end 13 of the catheter 10 in contact with the anastomosis of the vessel 42. The maintaining of the contact ensures that the solution $SOL_1$ does not flow back into the vessel 41.

FIG. 6A shows an example of a shape wherein the junction element 20 has an S-shaped profile. This shape allows for a good introduction of the junction element 20 into the vein of Marshall 42 while still offering a curved surface making it possible to hug the shape of the anastomosis 43.

FIG. 6B shows another example of a shape of a profile of the junction element 20. In this case, the junction element 20 has a circumference that decreases linearly. The appendix 20 has a substantially conical shape. This shape allows for a good adaptation of the junction element 20 in the vein of Marshall 42. The diameter and the position of the anastomosis of the vein of Marshall is subject to substantial anatomical variations. This solution therefore makes it possible to obtain an end that can be adapted to different anastomosis morphologies.

FIG. 6C shows another alternative shape of the profile of the appendix 20. This "hyperbole" shape makes it possible to provide the introduction of the distal portion of the catheter 20. It makes it possible to introduce a more substantial portion of the appendix into the vein of Marshall 42 than in the cases of FIGS. 6A and 6B. This embodiment is for example adapted if the vein of Marshall 42 has a complex, enlarged or abnormal anatomy.

According to an alternative embodiment, the junction element 20 comprises a portion 25 intended to penetrate into the vessel 42 having a contact surface with the vessel 42 extending over 1 mm to 2 cm, preferably 3 mm to 1 cm.

According to an embodiment, the junction element 20 has an outer diameter that is smaller than the outer diameter of the catheter 10 over a length of 1 mm to 2 cm, preferably from 3 mm to 1 cm.

According to an embodiment, the junction element 20 comprises a rounded end. This embodiment makes it possible to not damage or tear a body tissue during the passage thereof in the vessels.

According to an embodiment, the junction element 20 is made from a flexible material. It can, according to an example, be deformable in such a way as to adapt to the geometry of the anastomosis 43 of the vein of Marshall 42. It can be made from a plastic or elastic material. According to an embodiment, it is comprised of a polymer material or a silicone.

According to an embodiment, the material of the junction element 20 comprises an elasticity that is greater than a predefined threshold. The threshold is defined for example according to a % of the elasticity of the tissues present on the surface of the vessels in the myocardium, for example that of the coronary sinus. According to an embodiment, the elasticity of the junction element 20 is substantially close to the average elasticity of the tissues of the myocardium.

According to an embodiment, the material of the junction element 20 comprises a ductibility that allows for a slight deformation in order to ensure a sealed contact by cooperating with the geometry of an anastomosis.

According to another embodiment, the junction element 20 is made from a hard material in order to favor the introduction thereof.

Lumen of the Catheter

According to an example, the lumen $LU_1$ is coaxial to the catheter 10. An advantage is to be able to pass, for example, a guide that ensures the stability of the catheter 10 in a vessel 41, for example a blood vessel of the vein type such as the coronary sinus. Once the catheter 10 is positioned and stabilized, the guide can be withdrawn in such a way as to introduce in a second step the solution $SOL_1$.

According to an embodiment, the catheter can be deflected. The deflection is controlled by a proximal handle. The catheter can be, for example, guided using a proximal handle, this is referred to as a catheter rendered deflectable.

The catheter 10 is compatible with different types of guides that can circulate in a lumen of which the diameter is suitable for the passage thereof.

According to an embodiment, a guide can, indeed, be adapted in the objective to stabilize the catheter 10.

According to an embodiment, the diameter of the distal opening 17 formed by the connection element 20 can be adapted to the introduction of a treatment solution $SOL_1$ of the alcohol type, to a revelator and/or to the passage of a guide.

When a revelator or a marker is introduced, it makes it possible to improve the visibility of the positioning of the catheter 10 by means of a medical imaging system, such as an X-ray imaging system. By way of example, the first lumen $LU_1$ can be used to diffuse a volume of iodine within a vessel 41. An advantage is to improve the positioning of the catheter 10 in such a way that the channel 22 of the appendix is precisely facing the outlet opening out of the vessel 42 or inside the vessel 42, such as shown in the zone 43, FIG. 3A.

Advantageously, the injection of iodine by the coaxial lumen $LU_1$ makes it possible to carry out a venography of the coronary sinus in order to locate the vein of Marshall 42. This step can be carried out prior to the positioning of the junction element 20 with respect to the anastomosis 43, i.e. at the ostium of the vessel 42 and of the vessel 41. Then, the injection of alcohol into said vein 42 can be conducted with complete safety by a visual assistance conducted using an imaging system.

According to an embodiment, the first lumen $LU_1$ is adapted to receive an internal lumen $LU_2$ for the passage of an angioplasty balloon. According to an example, the lumen $LU_2$ can be considered as a catheter of small diameter that can be introduced into the lumen $LU_1$ in order to penetrate more distally in a vessel of low caliber.

According to another embodiment, the lumen $LU_1$ is adapted to the passage of an angioplasty balloon.

Figure 4:
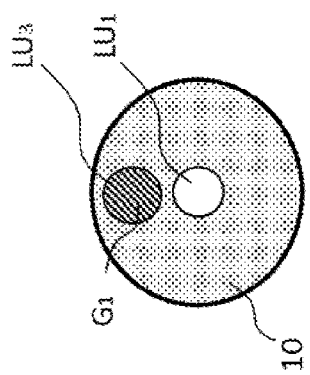
FIG. 4: a cross-section view along a lateral plane of an embodiment of a device of the invention.

According to an embodiment, the catheter 10 has a diameter comprised between 6 and 9 F allowing it to have at least one central lumen $LU_1$ but also according to another embodiment two lumens $LU_1$ and $LU_3$. FIG. 4 shows an embodiment wherein the catheter 10 comprises two lumens $LU_1$ and $LU_3$. A guide $G_1$ is introduced into the lumen $LU_3$ in such a way as to guide the catheter 10 and to maintain the catheter 10 in a stabilized position during the introduction of the solution $SOL_1$ into the lumen $LU_1$.

According to an embodiment, the device 1 of the invention comprises a sheath of a larger diameter than that of the catheter 10. Advantageously, the sheath allows for the guiding of the catheter 10 to the coronary sinus when it entails a treatment of the vein of Marshall. According to an embodiment, the sheath is an interventional cardiology sheath.

An advantage of the device 1 of the invention is to make it possible to ensure several functions with a single device. The function of guiding, the function of introducing a revelator such as iodine and the introducing of a treatment solution of a vessel, such as alcohol.

According to an embodiment, the invention relates to a lumen comprising an appendix 20 intended to be made secure within the catheter 10 into the coaxial lumen $LU_1$. FIG. 3B shows such a lumen $LU_2$ comprising an appendix 20. The lumen $LU_2$ can be, for example, positioned within the catheter 10 before the introduction thereof.

According to an embodiment, the catheter 1 comprises one or more collection electrodes arranged within the lumen $LU_1$. The electrode is arranged in such a way as to have a conductive portion protruding with respect to the opening 17 of the distal end of the appendix 20.

According to an embodiment, the catheter 10 comprises electrodes on the distal surface of the body of the catheter making it possible to record the electrical activity in the vessel 41.

According to an embodiment, the catheter can be deflected. The deflection is controlled by a proximal handle. The catheter can be, for example, guided using a proximal handle. This is referred to as a catheter rendered deflectable and therefore able to be oriented in order to facilitate the introduction into the coronary sinus then into the ostium of the vein of Marshall.

An advantage is to measure an electrical conductivity of a zone located in the vein of Marshall, in particular at the anastomosis 43. The electrode can be introduced from the proximal opening and be positioned for example by means of a guide at the distal end 17 of the appendix 20.

According to another example, the appendix 20 is made from a deformable material and can be compressed during the introduction thereof by the proximal end of the catheter 10 to arrive up to the distal end of the catheter 10 where it is hooked to the distal end of the catheter 10.

According to another aspect, the invention relates to a method of treatment of the vein of Marshall.

The method comprises:
- an introduction of a device 1 of the invention into the coronary sinus;
- an introduction of a solution of the revelator type, for example iodine, so as to improve the contrast of images acquired by an imaging system, said solution being introduced by the first lumen $LU_1$;
- a positioning of the catheter 10 in such a way as to position the distal outlet 17 of the junction element 20 at the anastomosis 43 of the vein of Marshall 42;
- a control of the positioning of the outlet 17 so that it opens out at the anastomosis of the vein of Marshall 42;
- an introduction of a treatment solution $SOL_1$ into the first lumen $LU_1$ so that it is conveyed into the anastomosis zone 43 and inside the vein of Marshall 42.

According to an embodiment, the treatment solution SOL is an alcohol solution. According to an embodiment, a test liquid, such as an iodine solution, is introduced prior to the treatment solution $SOL_1$ into the first lumen $LU_1$ so as to verify the seal of the contact between the appendix 20 and the wall of the coronary sinus 41, the wall of the vessel 42 or the zone forming the anastomosis of the vein of Marshall (vessel 42).

According to an embodiment, an introduction of an internal lumen $LU_2$ into the first lumen $LU_1$ makes it possible to deliver the solution of the revelator type as an alternative of its conveyance by the central lumen $LU_1$. In a second step, it is withdrawn so as to release the first lumen $LU_1$ so that the treatment solution SOL is introduced.

An advantage of the catheter 10 of the invention is to facilitate the chemical ablation of the zone comprising the anastomosis of the vein of Marshall and the vein itself. Indeed, the catheter 10 makes it possible to obtain a destruction of the muscular conduction tissue associated with the vein of Marshall. As specified hereinabove, the vein of Marshall and the muscular arborization thereof are involved in several ways in the process of atrial fibrillation.

The invention relates to the usage of the catheter for carrying out an alcoholization of the vein of Marshall. For this purpose, the catheter 10 is introduced into the anastomosis 43 of the vein of Marshall 42, the distal appendix 20 is then oriented to cooperate with the wall of the coronary sinus at the anastomosis zone. The outlet of the channel 23 is then oriented with respect to the anastomosis 43 of the vein of Marshall 42. The contact between the appendix and the wall of the vessel at the zone 43 provides the seal during the introduction of a volume of alcohol into the first lumen $LU_1$ in order to be introduced into the vein of Marshall 42. Once the catheter 10 is positioned, a volume of alcohol is introduced into the lumen $LU_1$. An alternative means is to use an angioplasty material with the aforementioned disadvantages of the prior art.

In a complementary and optional manner, a second volume of alcohol can be introduced within the vein of Marshall 42 from a device introduced into the first lumen $LU_1$. This embodiment makes it possible to inject a volume of alcohol inside the vein 42 and so as to go beyond the zone directly in the vicinity of the anastomosis zone 43. For example, the device introduced can be an angioplasty balloon.

Figure 8:
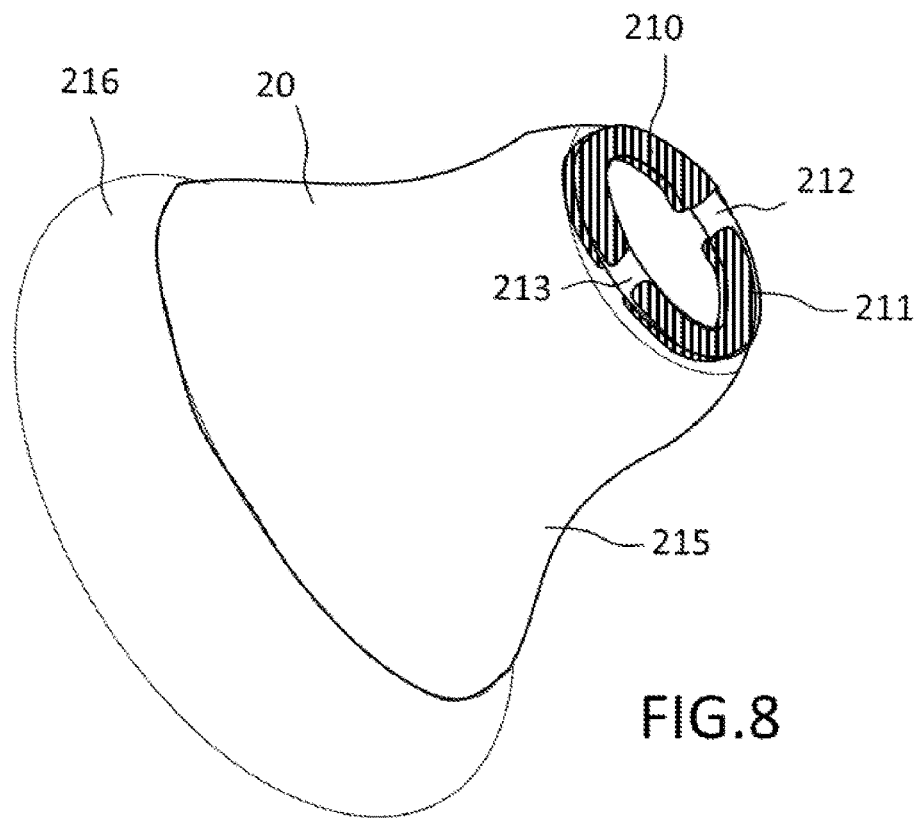
FIG. 8: an example of a junction element comprising distal electrodes for measuring an electric field.

FIG. 8 shows a junction element 20 comprising at the distal end 17 of the channel 22 an opening provided on the periphery thereof with at least two electrodes 210 and 211. According to an example, the electrodes 210 and 211 form a pair of electrodes, of which one reference electrode 210 and one working electrode 211. The two electrodes 210, 211 are for example, separated from one another by an electrical insulation 213 and 212. In the case where the electrodes form an arc of a circle at the distal end of the channel 22, the insulating portions 213 and 212 can also form a circular portion. The electrodes 210 and 211 can be extended inside the catheter 10 by at least one conductive element. The conductive elements can be guided, for example, within the catheter 10 by a lumen (not shown). The electric potential can thus be measured using a proximal connector of the catheter 10.

According to an example, the proximal material forming the electrodes 210, 212 can be a polished metal so as to not attack the tissues. It can alternatively be made from a polymer material into which a conductive powder is injected. Other conductive materials can be used according to other embodiments of the invention.

An advantage of this configuration is to measure the electric potential on a wall of a vessel 41, 42 at the anastomosis zone 43 or directly on a portion of a wall of a vessel 41 or 42. The catheter 10 being deformable from a proximal control, the catheter 10 can be oriented in such a way as to establish a contact between a wall of a vessel and the distal end thereof. An advantage is to be able to verify the electrical activity in the vessel 41 during a series of heartbeats. This verification makes it possible to validate or not the treatment to be conducted of said vessel 41.

The junction element 20 comprises a profile 215 adapted to cooperate with the shape of the anastomosis zone 43 in such a way as to carry out a border that favors the seal of this zone with respect to the zones upstream and downstream from the vessel 41 when the catheter 10 is positioned. According to an embodiment, the junction element 20 comprises a positioning ring 216 that has a circumference of which the radius can be greater than that of the catheter 10. An advantage of a positioning ring 216 is to form a sealed contact at the anastomosis zone 43. Advantageously, the sealed contact forms a ring around the anastomosis of the vessel 42. The positioning ring 216 thus makes it possible to secure the seal of the anastomosis zone 43 that has to be treated with a solution $SOL_1$.

According to an embodiment, the positioning ring 216 is a lip that forms a rounded edge on the circumference of the distal end of the catheter 10. The profile of the lip is convex in such a way as to favor firstly the contact of this part during the introduction of the junction element 20 in the anastomosis zone 43 in the direction of the vessel 42. The positioning ring 216 can form a crown, of the collar type. According to an embodiment, the collar 216 is movable. In this case, it can be adapted to the geometry of the anastomosis zone 43. Thus, an image carried out beforehand of the zone to be treated, for example by MRI or by a scanner, makes it possible to choose the junction element 20 when it is movable or makes it possible to choose the ring 216 when it is movable.

According to an embodiment, the positioning ring 216 is inflatable. The inflation is, for example, carried out using a lumen (not shown) internal to the catheter 10. Thus, the inflation is preferably carried out remotely. According to an embodiment, a lateral opening on the wall of the catheter 10 makes it possible to convey a volume of liquid or gas to inflate the positioning ring 216. When the positioning ring 216 is a balloon, the latter can be crimped in a groove of the catheter 10, alternatively the balloon can be glued or thermobonded on the wall of the catheter 10. The gluing can result from a melting of the material of the balloon in the body of the catheter.

According to an embodiment, the diameter of the junction element 20 decreases beyond the positioning ring 216. An advantage is to treat the anastomosis zone 43 without the catheter penetrating excessively into the vessel 42. Thus, the treatment can be effective in the anastomosis zone and not only in the vessel 42.

According to a protocol, the catheter 10 is positioned at the anastomosis zone 43. An inflation of the positioning ring 216 is carried out and a treatment of the zone is carried out using the injection of a volume of solution $SOL_1$ at this level. Then in a second step, the positioning ring 216 is deflated and the catheter 10 penetrates into the vessel 42 in order to treat the inside of the vessel 42 with the solution $SOL_1$. When successively the anastomosis zone 43 and the vessel 42 are treated, the catheter 10 is withdrawn.

Figure 9:
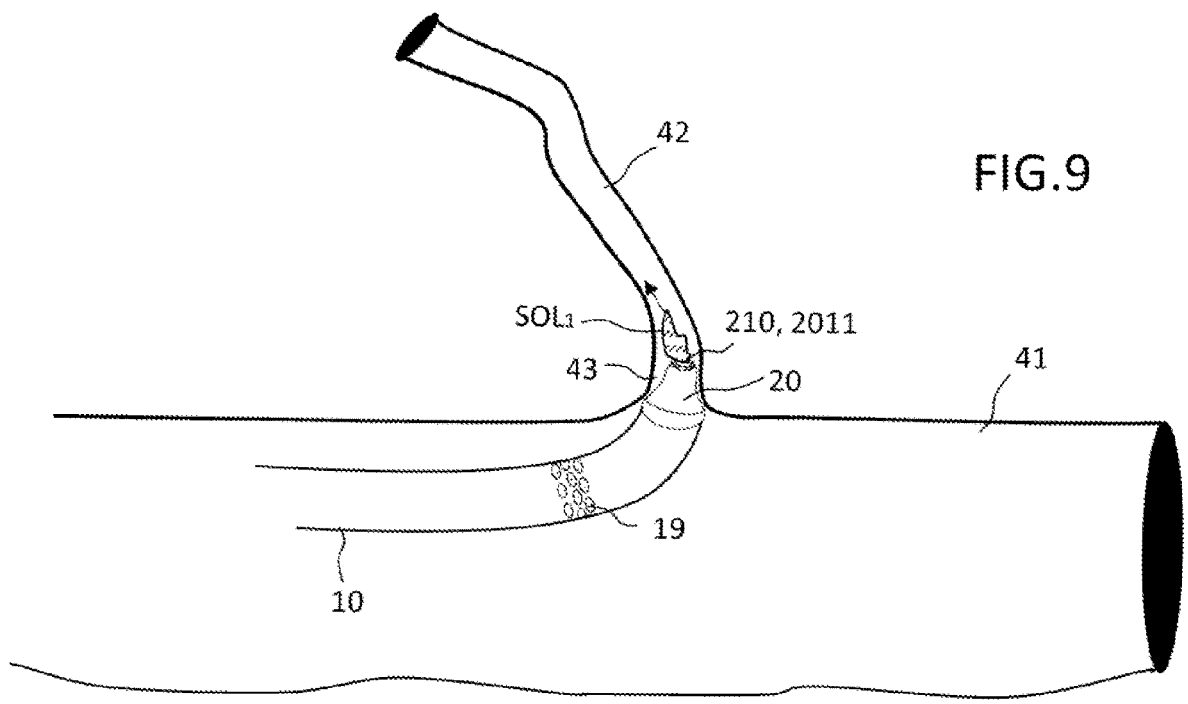
FIG. 9: an example of a device of the invention comprising a junction element comprising distal electrodes for measuring a first electric field and electrodes on the surface of the body of the catheter for measuring a second electric field.

FIG. 9 shows a catheter 10 provided with a junction element 20 at the distal end thereof. An operator can then control the orientation of the catheter 10 in such a way as to carry out a sufficient curvature to position the junction element 20 with regards to the anastomosis zone 43 until coming into contact with the wall of the vessels 41, 42 at the anastomosis zone 43. In the example of FIG. 9, the body of the catheter 10 is provided with electrodes 19 to measure the electrical activity in the vicinity of the anastomosis zone 43. An interest is to verify the electrical conductivity of the vessel 41 downstream or upstream from the anastomosis zone 43, according to how the catheter 10 entered the vessel 41.

Figure 10:
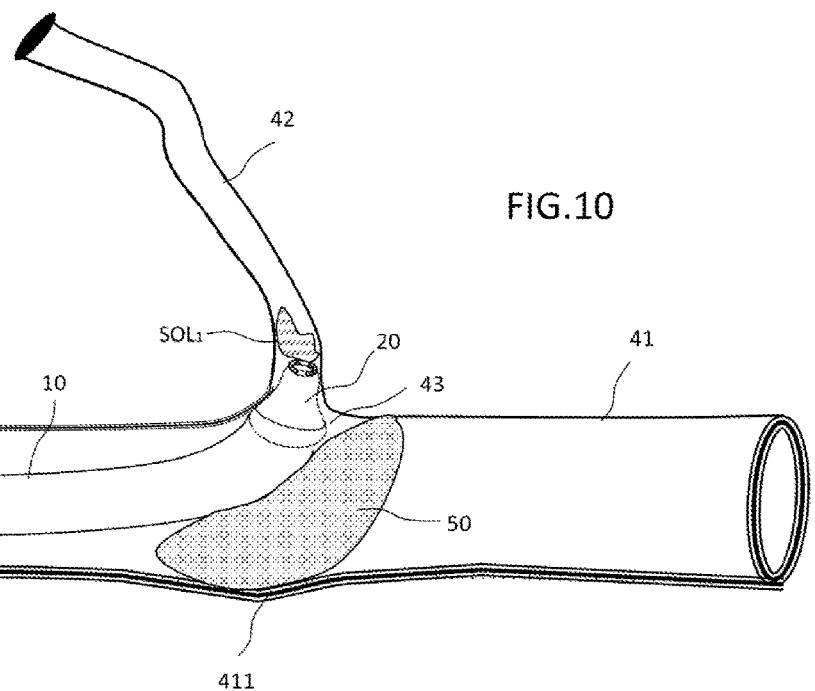
FIG. 10: an example of a device of the invention comprising a lateral balloon for sealing an anastomosis zone with regards to a zone of a vessel located downstream from the anastomosis zone.

FIG. 10 shows an example of a catheter 10 provided with a first lateral balloon 50. The lateral balloon 50 is inflated from a first lateral opening of the catheter 10 and from a first lumen (not shown) arranged inside the catheter 10 and opening out onto said lateral opening. According to an alternative, the inflation is carried out from a first lumen outside the catheter 10. The balloon 50 is inflated until a sealed border is formed between the zone downstream to the anastomosis zone 43 and the anastomosis zone 43. The balloon 50 can be inflated until the vessel 41 is obstructed.

The first balloon 50 makes it possible to improve the seal of a portion of the vessel 41 with regards to the anastomosis zone 43 to be treated. The inflation of the first balloon 50 is carried out until the vessel 41 is slightly deformed, here visible on the portion 411. The deformation of the vessel 41 makes it possible to improve the seal of the border formed due to the pressure exerted on the wall of the vessel 41. Furthermore, the balloon 50 makes it possible to stabilize the positioning of the catheter 10 when the junction element 20 is bearing on the walls of the vessels in particular in the anastomosis zone 43.

Figure 11:
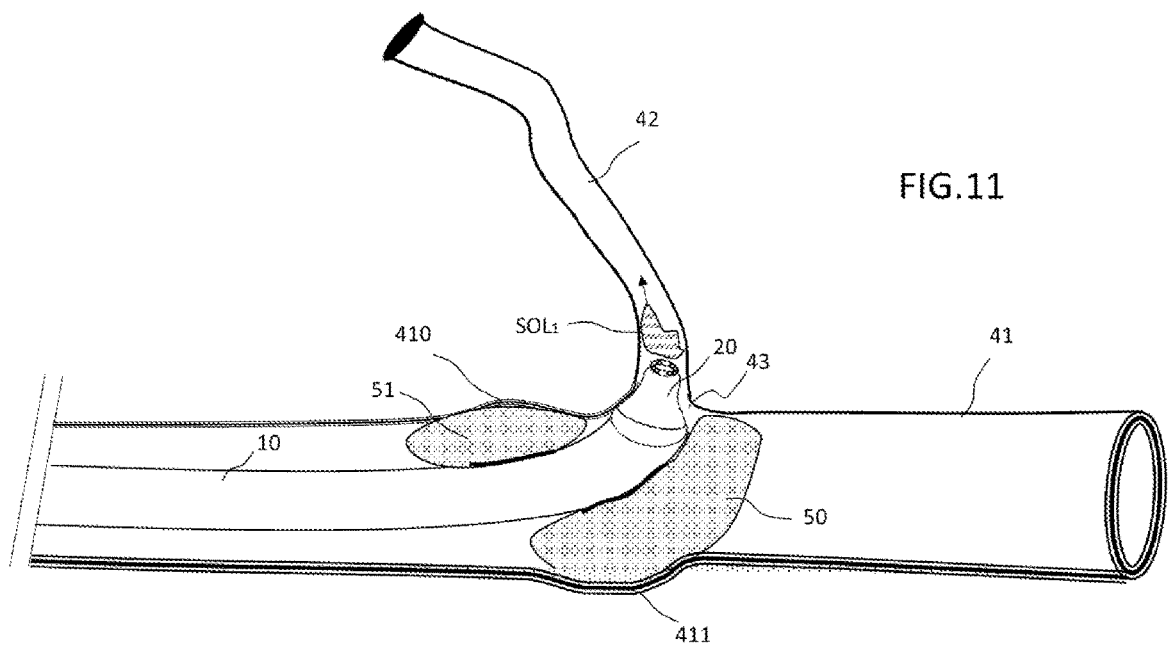
FIG. 11: an example of a device of the invention comprising lateral balloons in order to seal an anastomosis zone with regards to zones of a vessel located downstream and upstream from the anastomosis zone.

FIG. 11 shows an example of a catheter 10 provided with a first lateral balloon 50 and a second lateral balloon 51. The lateral balloon 51 is inflated from a second lateral opening of the catheter 10 and from a second lumen (not shown) arranged inside the catheter 10. According to an alternative, the inflation can be carried out from a second lumen outside the catheter 10. The balloon is inflated until a sealed border is formed between the upstream zone and the anastomosis zone 43. The positioning of the second lateral opening of the catheter intended to inflate the second balloon 51 is preferably arranged upstream from the first opening in the proximal direction. Preferably, this second opening is arranged at substantially 180° from the first opening on the wall of the catheter 10.

Thus, using two balloons 50, 51 makes it possible to define a sealed zone at the anastomosis zone 43 on the one hand with respect to the downstream zone of the anastomosis zone 43 and on the other hand with respect to an upstream zone of the anastomosis zone 43.

The second balloon 51 makes it possible to improve the seal of a portion of the vessel 41 with regards to the anastomosis zone 43 to be treated. Furthermore, the second balloon 51 makes it possible to stabilize the positioning of the catheter 10 when the junction element 20 is bearing on the walls of the vessels 41, 42, in particular in the anastomosis zone 43. The balloons 50, 51 can be fixed to the surface of catheter 10.

According to a configuration, a portion of the outer wall of the catheter 10 forms a wall of the inflated volume. According to an example, the balloons are circumferential and form rings or toroids around the catheter 10. This is particularly interesting for the balloon 51 so that it completely obstructs the vessel 41 downstream from the anastomosis zone 43. According to another example, the balloons extend partially at the circumference of the body of the catheter 10.

In the case of FIG. 11, the portion 410 of the vessel 41 located upstream from the anastomosis zone 43 is deformed and the zone 411 of the vessel 41 located downstream from the anastomosis zone 43 is also deformed. This deformation aims to reinforce the seal of the treated zone comprising the anastomosis zone 43. So as to finish with a slight deformation of the vessel, the balloon is inflated sufficiently in order to obtain this result.

The invention claimed is:

1. A medical device comprising:
   a deformable catheter and of which the deformation can be controlled, said deformable catheter comprising a first lumen for injection of a first volume of a treatment solution, the first lumen having an opening at a distal end of the catheter;
   a junction element extending away from the first lumen at an end of the catheter, the junction element comprising an outer diameter at a distal end thereof that is less than an outer diameter of the catheter, said junction element being arranged to cooperate with an anastomosis zone of a first vessel with a second vessel,
   wherein the junction element is adapted to cooperate with said anastomosis zone to form a sealed contact therebetween, and
   wherein the junction element comprises a positioning ring arranged to form a bearing surface in contact with the anastomosis zone, an outer diameter of the positioning ring being greater than the outer diameter of the catheter.

2. The medical device according to claim 1, wherein the junction element is arranged to form a sealed circumferential contact with an anastomosis zone of two vessels.

3. The medical device according to claim 1, wherein the junction element comprises two electrodes arranged at the distal end thereof.

4. The medical device according to claim 1, wherein a body of the catheter comprises a plurality of electrodes arranged on at least one portion of a circumference thereof.

5. The medical device according to claim 1, further comprising a first positioning balloon arranged on a wall of the catheter and arranged to create a first sealed border with a wall of the first vessel.

6. The medical device according to claim 5, further comprising a second positioning balloon arranged on the wall of the catheter and arranged to create a second sealed border with a portion of the wall of the first vessel.

7. The medical device according to claim 1, wherein the junction element comprises a portion having a circumferential edge arranged to bear against walls of a vessel.

8. The medical device according to claim 1, wherein the junction element comprises a profile that has a concave or straight portion extending from the distal end of the catheter in the direction of the distal end of the junction element.

9. The medical device according to claim 1, wherein the junction element comprises a profile that has a substantial conical shape.

10. The medical device according to claim 1, wherein the junction element comprises a rounded distal end.

11. The medical device according to claim 1, wherein the junction element comprises a profile of which an outer diameter varies so as to form a sealed wall between the first vessel and the second vessel when the distal end of the catheter is positioned bearing against a wall of the second vessel.

12. The medical device according to claim 1, wherein the catheter comprises at least one electrode arranged at a distal surface of a body of the catheter making it possible to record an electrical activity in the second vessel.

13. The medical device according to claim 1, wherein the first lumen comprises a diameter comprised between 2 F and 5 F.

14. A medical device comprising:
   a deformable catheter and of which the deformation can be controlled, said deformable catheter comprising a first lumen for injection of a first volume of a treatment solution, the first lumen having an opening at a distal end of the catheter;
   a junction element extending away from the first lumen at an end of the catheter, the junction element comprising an outer diameter at a distal end thereof that is less than an outer diameter of the catheter, said junction element being arranged to cooperate with an anastomosis zone of a first vessel with a second vessel,
   wherein the junction element is adapted to cooperate with said anastomosis zone to form a sealed contact therebetween, and wherein the junction element comprises a profile that has a concave portion extending from the distal end of the catheter in a direction of the distal end of the junction element.

15. A medical device comprising:
- a deformable catheter and of which the deformation can be controlled, said deformable catheter comprising a first lumen for injection of a first volume of a treatment solution, the first lumen having an opening at a distal end of the catheter;
- a junction element extending away from the first lumen at an end of the catheter, the junction element comprising an outer diameter at a distal end thereof that is less than an outer diameter of the catheter, said junction element being arranged to cooperate with an anastomosis zone of a first vessel with a second vessel, said second vessel being a vein of Marshall, wherein the junction element is adapted to cooperate with said anastomosis zone (a) to form a sealed contact therebetween and (b) to maintain said sealed contact between the anastomosis zone and the junction element during introduction of the first volume of the treatment solution into said vein of Marshall.

\* \* \* \* \*